US012788847B2

(12) United States Patent
Lin et al.

(10) Patent No.: US 12,788,847 B2
(45) Date of Patent: *Nov. 10, 2026

(54) METHODS FOR PREPARING TISSUE GRAFTS WITH ANTIMICROBIAL PROPERTIES

(71) Applicant: Rutgers, The State University of New Jersey, New Brunswick, NJ (US)

(72) Inventors: Sheldon S. Lin, Chatham, NJ (US); Joseph Benevenia, Montclair, NJ (US); Michael J. Vives, Newark, NJ (US); Pradeep Kumar, Bloomfield, NJ (US); David Alland, Bernardsville, NJ (US); James Patrick O'Connor, Fanwood, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 1168 days.

This patent is subject to a terminal disclaimer.

(21) Appl. No.: 17/540,856

(22) Filed: Dec. 2, 2021

(65) Prior Publication Data

US 2022/0088271 A1 Mar. 24, 2022

Related U.S. Application Data

(63) Continuation-in-part of application No. 15/425,617, filed on Feb. 6, 2017, now Pat. No. 11,224,678.

(60) Provisional application No. 62/293,064, filed on Feb. 9, 2016.

(51) Int. Cl.

*A61L 27/36* (2006.01)
*A01N 59/16* (2006.01)
*A01P 1/00* (2006.01)

(52) U.S. Cl.

CPC .......... *A61L 27/3687* (2013.01); *A01N 59/16* (2013.01); *A01P 1/00* (2021.08); *A61L 27/3604* (2013.01); *A61L 27/3608* (2013.01); *A61L 27/3612* (2013.01)

(58) Field of Classification Search

CPC .................................................. A61L 27/3687
See application file for complete search history.

(56) References Cited

U.S. PATENT DOCUMENTS

| | | | |
|---|---|---|---|
| 4,759,445 | A | 7/1988 | McVay |
| 4,813,210 | A | 3/1989 | Masuda et al. |
| 5,454,886 | A | 10/1995 | Burrell et al. |
| 5,520,664 | A | 5/1996 | Bricault, Jr. et al. |
| 5,906,825 | A | 5/1999 | Seabrook, Jr. et al. |
| 6,013,106 | A | 1/2000 | Tweden et al. |
| 6,113,636 | A | 9/2000 | Ogle |
| 6,254,294 | B1 | 7/2001 | Muhar |
| 6,337,052 | B1 | 1/2002 | Rosenwasser |
| 9,238,090 | B1 | 1/2016 | Fette |
| 11,224,678 | B2 | 1/2022 | Benevenia et al. |
| 12,178,205 | B2 | 12/2024 | Benevenia et al. |
| 2007/0185026 | A1 | 8/2007 | Walsh et al. |
| 2007/0207186 | A1 | 9/2007 | Scanlon et al. |
| 2011/0140316 | A1 | 6/2011 | Bagga et al. |
| 2013/0028981 | A1 | 1/2013 | Gratzer |
| 2013/0277242 | A1 | 10/2013 | Mori |
| 2013/0280223 | A1 | 10/2013 | Owens et al. |
| 2014/0021208 | A1 | 1/2014 | Anti et al. |
| 2014/0147487 | A1 | 5/2014 | Walls |
| 2014/0271779 | A1 | 9/2014 | Bagga et al. |
| 2015/0004249 | A1 | 1/2015 | Lin et al. |
| 2015/0239640 | A1 | 8/2015 | Smith et al. |
| 2015/0351893 | A1 | 12/2015 | Smith et al. |
| 2017/0106119 | A1 | 4/2017 | Skinner et al. |
| 2017/0224871 | A1 | 8/2017 | Benevenia et al. |
| 2019/0274809 | A1 | 9/2019 | Kapec et al. |
| 2019/0358366 | A1 | 11/2019 | Zawko et al. |
| 2020/0207830 | A1 | 7/2020 | Feuerbach et al. |
| 2021/0251215 | A1 | 8/2021 | Benevenia et al. |
| 2021/0308328 | A1 | 10/2021 | Fette |

FOREIGN PATENT DOCUMENTS

| | | | |
|---|---|---|---|
| JP | 2001-523527 | A | 11/2001 |
| JP | 2015113299 | A | 6/2015 |
| WO | 08032928 | A1 | 3/2008 |

OTHER PUBLICATIONS

Qayyum et al: "The Antimicrobial Activity of Different Zinc Salts", Proceedings S.Z.P.G.M.I., 1998, vol. 12[1-2], pp. 8-12.
Delloye, et al: "Bone Allografts: What They Can Offer and What They Cannot", 2007, The Bone & Joint Journal, vol. 39, No. 5, pp. 574-579.
Maral, et al: "Effectiveness of Human Amnion Preserved Long-Term in Glycerol as a Temporary Biological Dressing", Burns, 1999, 25, pp. 625-635.
Faiz, et al: "Efficacy of Zinc as Antibacterial Agent Against Enteric Bacterial Pathogens", J. Ayub Med Coll Abbottabad, 2011, vol. 23, No. 2, pp. 20.
Aho, et al: "Clinical Use of Bone Allografts", Annals of Medicine, 1993, 25:4, pp. 403-412, DOI: 10.3109/07853899309147303.
Lord, et al: "Infection in Bone Allografts", Incidence, Nature, and Treatment, The Journal of Bone and Joint Surgery,. Mar. 1988, vol. 70, pp. 369-376.
Muscolo, et al: "The Use of a Bone Allograft for Reconstruction after Resection of Giant-Cell Tumor Close to the Knee", The Journal of Bone and Joint Surgery, Nov. 1993, vol. 75, No. 11, pp. 1656-1662.
Tomford, et al: "Frozen Musculoskeletal Allografts, A Study of the Clinical Incidence and Causes of Infection Associated with Their Use", The Journal of Bone and Joint Surgery, Sep. 1990, vol. 72, No. 8, pp. 1137-1143.

(Continued)

*Primary Examiner* — Kevin Joyner
(74) *Attorney, Agent, or Firm* — FOX ROTHSCHILD LLP

(57) ABSTRACT

The present invention is a method for producing allograft tissue by applying an antimicrobial solution to allograft tissue. The antimicrobial solution exhibits antimicrobial activity to make allograft resistant to microbial organisms, such as a bacterium.

15 Claims, No Drawings

(56) References Cited

OTHER PUBLICATIONS

Mankin, et al: "Infection in Massive Bone Allografts", Clinical Orthopaedics and Related Research, 2005, No. 432, pp. 210-216.
Fuierer et al: "A Mineralization Adsorption and Mobility Study of Hydroxyapatite Surfaces in the Presence of Zinc and Magnesium Ions", Langmuir, 1994, vol. 10, No. 12, pp. 4721-4725.

METHODS FOR PREPARING TISSUE GRAFTS WITH ANTIMICROBIAL PROPERTIES

CROSS-REFERENCE TO RELATED APPLICATIONS

The present application is a continuation-in-part of U.S. Nonprovisional patent application Ser. No. 15/425,617, filed Feb. 6, 2017, which claims the benefit of priority under 35 U.S.C. § 119(e) to U.S. Provisional Patent Application No. 62/293,064, filed Feb. 9, 2016. The present application is also a continuation-in-part of U.S. Nonprovisional patent application Ser. No. 17/307,493, filed May 4, 2021, now U.S. Pat. No. 12,178,205, which claims the benefit of priority under 35 U.S.C. § 119(e) to U.S. Provisional Patent Application No. 63/019,525, filed May 4, 2020.

FIELD

The present invention relates in general to a method of preparing a tissue graft to provide improved antimicrobial properties and, in particular, to a method of using a solution of an antimicrobial composition to make allograft resistant to microbial organisms, such as *Mycobacterium tuberculosis.*

BACKGROUND

Surgeons are frequently faced with reconstruction challenges caused by bone loss. Although autologous bone is the gold standard for bone restoration, donor site morbidity and limited bone volume have led to increased utilization of allograft bone. Approximately 800,000 bone allograft transplantations are performed yearly in the United States, making bone the second most commonly transplanted tissue as described in Boyce et al. Although bone allograft generally restores bone mass, complications such as graft-host nonunion, fracture, and graft infection are not infrequent as described in Aho A J (Ann Med. 1993; 25:403-412).

Allograft-associated infection often requires removal of infected bone and extensive debridement of the affected site with substantial patient morbidity. The use of a bone allograft for reconstruction after resection of giant-cell tumor close to the knee (J Bone Joint Surg Am. 1993; 75:1656-1662). Most of these allograft-associated infections can occur early, such as within four months (Lord et al., J Bone Joint Surg Am. 1988; 70:369-376). Despite extended antibiotic prophylaxis, the reported incidence remains at 4% to 12% (Mankin H J et al. Clin Orthop Relat Res. 2005; 432:210-216). Like metallic implants, allografts act as highly porous, non-cellular, and avascular foreign bodies prone to bacterial adhesion.

Approaches have been described for depositing antimicrobial elemental metal and/or metal compounds within a medical article. U.S. Pat. No. 6,113,636 describes chemical, photochemical, and electrochemical processes for depositing elemental metal on and in a biocompatible material such as tissue. Three approaches are described for associating elemental metal with tissue and other biocompatible materials under relatively mild conditions. A first approach involves the reaction of metal solutions with a chemical reductant, such as an unreacted crosslinking agent, which may be present in or added to the tissue. A second approach involves photo-reduction of metal compounds in the presence of a biocompatible material. Finally, elemental metal can be deposited by electrochemical reduction. However, chemical or electrochemical processing can have the shortcomings of being harmful to the tissue and require cumbersome or expensive manufacturing.

Thus, there is a need for methods for processing tissue grafts without chemical or electrochemical processing to obtain tissue grafts resistant to microbial organisms.

SUMMARY

This disclosure addresses the need mentioned above in a number of aspects. In one aspect, this disclosure provides a method for preparing a tissue graft. The method comprises: providing a tissue graft; and applying to the tissue graft an antimicrobial solution comprising a zinc compound by contacting the tissue graft with the antimicrobial solution, thereby causing the zinc compound to directly associate with the tissue graft and modify the surface of the allograft tissue, wherein the antimicrobial solution exhibits antimicrobial activity of inhibiting or controlling growth of *Mycobacterium tuberculosis* in the tissue graft and provides deep tissue cleaning.

In some embodiments, the zinc compound is selected from the group consisting of zinc chloride, zinc sulfate, zinc phosphate, zinc carbonate, and zinc nitrate, zinc chlorate, zinc chromate, and combinations thereof. In some embodiments, the zinc compound is zinc chloride. In some embodiments, the antimicrobial solution comprises $Zn^{2+}$ ions.

In some embodiments, the zinc compound is a zinc salt selected from zinc acetate, zinc formate, zinc propionate, zinc gluconate, bis(maltolato)zinc, zinc acexamate, zinc aspartate, bis(maltolato)zinc(II) [Zn(ma)2], bis(2-hydroxy-pyridine-N-oxido)zinc(II) [Zn(hpo)2], bis(allixinato)Zn(II) [Zn(alx)2], bis(6-methylpicolinato)Zn(II) [Zn(6mpa)2], bis (aspirinato)zinc(II), bis(pyrrole-2-carboxylato) zinc [Zn(pc) 2], bis(alpha-furonic acidato)zinc [Zn(fa)2], bis(thiophene-2-carboxylato) zinc [Zn(tc)2], bis(thiophene-2-acetato)zinc [Zn(ta)2], (N-acetyl-L-cysteinato) Zn(II) [Zn(nac)], zinc(II)/ poly(γ-glutamic acid) [Zn(γ-pga)], bis(pyrrolidine-N-dithiocarbamate)zinc(II) [$Zn(pdc)_2$], zinc(II) L-lactate [$Zn(lac)_2$], zinc(II) D-(2)-quinic acid [$Zn(qui)_2$], bis(1,6-dimethyl-3-hydroxy-5-methoxy-2-pentyl-1,4-dihydropyridine-4-thionato)zinc(II) [Zn(tanm)2], β-alanyl-L-histidinato zinc(II) (AHZ) and combinations thereof.

In some embodiments, the tissue graft with the antimicrobial solution comprises soaking, rinsing, or washing the tissue graft in the antimicrobial solution.

In some embodiments, the tissue graft comprises a tissue selected from allograft bone, autograft bone, xenograft bone, allograft cartilage, amniotic tissue, ligament tissue, tendon tissue, porous tissue, soft tissue, and a combination thereof. In some embodiments, the tissue graft comprises an allograft tissue. In some embodiments, the allograft tissue comprises allograft bone. In some embodiments, the tissue graft comprises amniotic tissue. In some embodiments, the tissue graft comprises allograft cartilage.

In some embodiments, the step of applying comprises applying to the allograft tissue the antimicrobial solution comprising from about 1% to about 20% zinc chloride by soaking, rinsing, or washing the tissue graft in the antimicrobial solution for about 1 hour to about 24 hours.

In some embodiments, the step of applying comprises applying to the allograft tissue the antimicrobial solution comprising from about 5% to about 10% zinc chloride by soaking, rinsing, or washing the tissue graft in the antimicrobial solution for about 1 hour to about 24 hours.

In some embodiments, the antimicrobial solution further comprises a pharmaceutically acceptable vehicle, excipient, diluent, or adjuvant.

In another aspect, this disclosure also provides a tissue graft prepared by a method as disclosed herein. In some embodiments, the tissue graft is penetrated by the antimicrobial solution and comprises a surface of the tissue graft modified by the zinc compound. In some embodiments, the tissue graft comprises a tissue selected from allograft bone, autograft bone, xenograft bone, allograft cartilage, amniotic tissue, ligament tissue, tendon tissue, porous tissue, soft tissue, and a combination thereof. In some embodiments, the tissue graft comprises an allograft tissue. In some embodiments, the allograft tissue comprises allograft bone. In some embodiments, the tissue graft comprises amniotic tissue. In some embodiments, the tissue graft comprises allograft cartilage.

In yet another aspect, this disclosure provides a kit comprising a tissue graft as disclosed herein.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

DETAILED DESCRIPTION

This disclosure relates to a method for preparing a tissue graft (e.g., allograft tissue, autograft tissue, xenograft tissue) by inhibiting the growth of a bacterium, such as *Mycobacterium tuberculosis*, in a tissue graft. In one aspect, this disclosure relates to a method for preparing a tissue graft comprising mechanically applying to the tissue graft an antimicrobial solution having an antimicrobial activity to the microbial organism.

In some embodiments, the method comprises: providing a tissue graft; and applying to the tissue graft an antimicrobial solution comprising a zinc compound by contacting the tissue graft with the antimicrobial solution, thereby causing the zinc compound to directly associate with the tissue graft and modify the surface of the allograft tissue, wherein the antimicrobial solution exhibits antimicrobial activity of inhibiting or controlling growth of a bacterium, i.e., *Mycobacterium tuberculosis*, in the tissue graft and provides deep tissue cleaning.

In some embodiments, the tissue graft with the antimicrobial solution comprises soaking, rinsing, or washing the tissue graft in the antimicrobial solution.

The term "antimicrobial activity" means in the context of the present invention that the antimicrobial of the invention is active in inhibiting, controlling, or combating microbial organisms, including fungal organisms and/or bacterial organisms, such as gram-positive and gram-negative bacteria. The antimicrobial activity can occur after the allograft is implanted into the body.

In some embodiments, the antibacterial activity is the activity for bacterium selected from the tuberculosis complex microorganisms (e.g., *Mycobacterium tuberculosis., Mycobacterium bovis, Mycobacterium africanum*), *Pseudomonas aeruginosa, Staphylococcus aureus, Aspergillus brasiliensis* spores, and *Escherichia coli.*

Examples of zinc compounds suitable for use in the antimicrobial solution may include inorganic zinc compounds, such as mineral acid zinc salts. Examples of inorganic zinc compounds include, but are not limited to, zinc chloride, zinc sulfate, zinc phosphate, zinc carbonate, and zinc nitrate, zinc chlorate, zinc chromate, or combinations thereof.

Examples of zinc compounds suitable for use in the antimicrobial solution can also be zinc salts of organic acids. Examples of organic acid zinc salts include, but are not limited to, zinc acetate, zinc formate, zinc propionate, zinc gluconate, bis(maltolato)zinc, zinc acexamate, zinc aspartate, bis(maltolato)zinc(II) [Zn(ma)2], bis(2-hydroxypyridine-N-oxido)zinc(II) [Zn(hpo)2], bis(allixinato)Zn(II) [Zn(alx)2], bis(6-methylpicolinato)Zn(II), [Zn(6mpa)2], bis(aspirinato)zinc(II), bis(pyrrole-2-carboxylato)zinc [Zn(pc)2], bis(alpha-furonic acidato)zinc [Zn(fa)2], bis(thiophene-2-carboxylato)zinc [Zn(tc)2], bis(thiophene-2-acetato)zinc [Zn(ta)2], (N-acetyl-L-cysteinato)Zn(II) [Zn(nac)], zinc(II)/poly(γ-glutamic acid) [Zn(γ-pga)], bis(pyrrolidine-N-dithiocarbamate)zinc(II) $[Zn(pdc)_2]$, zinc(II) L-lactate $[Zn(lac)_2]$, zinc(II) D-(2)-quinic acid $[Zn(qui)_2]$, bis(1,6-dimethyl-3-hydroxy-5-methoxy-2-pentyl-1,4-dihydropyridine-4-thionato)zinc(II)[Zn(tanm)2], β-alanyl-L-histidinato zinc(II) (AHZ), or the like, or combinations thereof. In another embodiment, the organic acid of zinc salt is a naturally occurring fatty acid.

In some embodiments, the antimicrobial solution comprises $Zn^{2+}$ ions.

In some embodiments, zinc compounds can be used in the antimicrobial solution in concentrations of about 1 mM to about 100 mM (e.g., 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 mM). In one embodiment, concentrations of zinc chloride of about 1 mM to about 20 mM (e.g., 1, 2, 3, 4, 5, 6, 7, 8, 9, 10, 11, 12, 13, 14, 15, 16, 17, 18, 19, 20 mM) can be used as the antimicrobial solution.

In some embodiments, the step of applying comprises applying to the allograft tissue the antimicrobial solution comprising from about 1% to about 20% (e.g., 1%, 2%, 3%, 4%, 5%, 6%, 7%, 8%, 9%, 10%, 11%, 12%, 13%, 14%, 15%, 16%, 17%, 18%, 19%, 20%)zinc compound (e.g., zinc chloride) by soaking, rinsing, or washing the tissue graft in the antimicrobial solution for about 1 hour to about 24 hours (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours).

In some embodiments, the step of applying comprises applying to the allograft tissue the antimicrobial solution comprising from about 5% to about 15% (e.g., 5%, 6%, 7%, 8%, 9%, 10%, 11%, 12%, 13%, 14%, 15%)zinc compound (e.g., zinc chloride) by soaking, rinsing, or washing the tissue graft in the antimicrobial solution for about 1 hour to about 24 hours (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours).

In some embodiments, the step of applying comprises applying to the allograft tissue the antimicrobial solution comprising from about 5% to about 10% (e.g., 5%, 6%, 7%, 8%, 9%, 10%) zinc compound (e.g., zinc chloride) by soaking, rinsing, or washing the tissue graft in the antimicrobial solution for about 1 hour to about 24 hours (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours).

In some embodiments, the tissue graft comprises a tissue selected from allograft bone, autograft bone, xenograft bone, allograft cartilage, amniotic tissue, ligament tissue, tendon tissue, porous tissue, soft tissue, and a combination thereof. In some embodiments, the tissue graft comprises an allograft tissue. In some embodiments, the allograft tissue comprises allograft bone. In some embodiments, the tissue graft comprises amniotic tissue. In some embodiments, the tissue graft comprises allograft cartilage.

Alternatively, allograft bone was rinsed with the antimicrobial solution such as by the Shake Flask Method (ASTM E2149). For example, the allograft bone can be rinsed in the antimicrobial solution for from about 45 minutes to about 120 minutes.

In some embodiments, the antimicrobial solution further comprises a pharmaceutically acceptable vehicle, excipient, diluent, or adjuvant.

For purposes of the following description, allograft bone is referred to as an exemplary tissue that may be processed according to the present method. However, those skilled in the art will recognize that other tissues, including but not limited to autograft bone, xenograft bone, allograft cartilage, allograft amniotic tissue, other porous tissues, synthetic porous materials, and various soft tissues, may be processed according to the principles defined herein, without departing from the spirit of the invention exemplified herein by reference to allograft bone material. Suitable allograft cartilage can be allograft cartilage manufactured by ANTHREX as BioCartilage®. In one embodiment, ligament or a tendon.

In some embodiments, the patient is a mammalian animal, e.g., a human.

In some embodiments, the method as disclosed herein can be used in combination with an allograft method, autograft method, xenograft method, alloplastic graft method, or orthopedic biocomposite method.

In another aspect, this disclosure also provides a tissue graft prepared by a method as disclosed herein. In some embodiments, the tissue graft is penetrated by the antimicrobial solution and comprises a surface of the tissue graft modified by the zinc compound. In some embodiments, the tissue graft comprises a tissue selected from allograft bone, autograft bone, xenograft bone, allograft cartilage, amniotic tissue, ligament tissue, tendon tissue, porous tissue, soft tissue, and a combination thereof. In some embodiments, the tissue graft comprises an allograft tissue. In some embodiments, the allograft tissue comprises allograft bone. In some embodiments, the tissue graft comprises amniotic tissue. In some embodiments, the tissue graft comprises allograft cartilage.

In yet another aspect, this disclosure provides a kit comprising a tissue graft as disclosed herein. In some embodiments, the kit also includes one or more additional agents (e.g., an antimicrobial solution) contained in the same or different container from the tissue graft. For example, the kit may include a tissue graft provided in a separate container or a separate compartment from the additional agents. In some embodiments, the kit may include informational material. The informational material can be descriptive, instructional, marketing or other material that relates to the tissue graft as prepared by the disclosed methods.

As used herein, a "subject," "subject," or "individual" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental animal or animal suitable as a disease model.

As used herein, the term "pharmaceutically acceptable" refers to a material, such as a carrier or diluent, which does not abrogate the biological activity or properties of the antimicrobial solution, and is relatively non-toxic, i.e., the material may be administered to an individual without causing undesirable biological effects or interacting in a deleterious manner with any of the components of the composition in which it is contained.

As used herein, the term "contacting," when used in reference to any set of components, includes any process whereby the components to be contacted are mixed into the same mixture (for example, are added into the same compartment or solution), and does not necessarily require actual physical contact between the recited components. The recited components can be contacted in any order or any combination (or sub-combination) and can include situations where one or some of the recited components are subsequently removed from the mixture, optionally prior to addition of other recited components. For example, "contacting A with B and C" includes any and all of the following situations: (i) A is mixed with C, then B is added to the mixture; (ii) A and B are mixed into a mixture; B is removed from the mixture, and then C is added to the mixture; and (iii) A is added to a mixture of B and C.

As used herein, the term "in vitro" refers to events that occur in an artificial environment, e.g., in a test tube or reaction vessel, in cell culture, etc., rather than within a multi-cellular organism.

As used herein, the term "in vivo" refers to events that occur within a multi-cellular organism such as a non-human animal.

It is noted here that, as used in this specification and the appended claims, the singular forms "a," "an," and "the" include plural reference unless the context clearly dictates otherwise.

The terms "including," "comprising," "containing," or "having" and variations thereof are meant to encompass the items listed thereafter and equivalents thereof as well as additional subject matter unless otherwise noted.

The phrases "in one embodiment," "in various embodiments," "in some embodiments," and the like are used repeatedly. Such phrases do not necessarily refer to the same embodiment, but they may unless the context dictates otherwise.

The terms "and/or" or "/" means any one of the items, any combination of the items, or all of the items with which this term is associated.

The word "substantially" does not exclude "completely," e.g., a composition which is "substantially free" from Y may be completely free from Y. Where necessary, the word "substantially" may be omitted from the definition of the present disclosure.

As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Unless indicated otherwise herein, the term "about" is intended to include values, e.g., weight percents, proximate to the recited range that are equivalent in terms of the functionality of the individual ingredient, the composition, or the embodiment.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

As used herein, the term "each," when used in reference to a collection of items, is intended to identify an individual item in the collection but does not necessarily refer to every item in the collection. Exceptions can occur if explicit disclosure or context clearly dictates otherwise.

The use of any and all examples, or exemplary language (e.g., "such as") provided herein, is intended merely to better illuminate the invention and does not pose a limitation on the scope of this disclosure unless otherwise claimed. No language in the specification should be construed as indicating any non-claimed element as essential to the practice of the invention. When used in this document, the term "exemplary" is intended to mean "by way of example" and is not intended to indicate that a particular exemplary item is preferred or required.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise.

In cases in which a method comprises a combination of steps, each and every combination or sub-combination of the steps is encompassed within the scope of the disclosure, unless otherwise noted herein.

Each publication, patent application, patent, and other reference cited herein is incorporated by reference in its entirety to the extent that it is not inconsistent with the present disclosure. Publications disclosed herein are provided solely for their disclosure prior to the filing date of the present disclosure. Nothing herein is to be construed as an admission that the present invention is not entitled to antedate such publication by virtue of prior invention. Further, the dates of publication provided may be different from the actual publication dates, which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Example 1

Materials and Methods

A suspension of test organism *Staphylococcus aureus* (ATCC 6538) was obtained by adding colonies on tryptic soy agar and 5% Sheep Blood (BAP) with incubation parameters of 35° C.-37° C., aerobic in 0.85% saline to match a 3.0 McFarland standard. The suspension was exposed to a test substance of zinc chloride at specified concentrations of 0.1%, 0.3%, and 0.5% from a 1% stock solution at specified exposure times of 10 minutes, 2 hours, 6 hours, and 24 hours at a temperature of 37±1° C. (37.2° C.).

Latheen broth and 1% sodium bicarbonate (9.9 mL) were used as a neutralizer. After exposure, an aliquot of the suspension was transferred to the neutralizer and was assayed for survivors. Tables 1-3 show the results of the controls used in this example.

TABLE 1

| Control Results | | |
|---|---|---|
| | Type of Control | Results |
| Purity | *Staphylococcus aureus* (ATCC 6538) | Pure |
| | Neutralizer Sterility Control | No Growth |

TABLE 2

| Test Population Control Results | | | | | |
|---|---|---|---|---|---|
| | | Results | | | |
| Test Organism | Timepoint | CFU/mL | Log10 | Average Log10 | Geometric Mean |
| *Staphylococcus aureus* (ATCC 6538) | $T_0$ | $3.5 \times 10^6$ | 6.54 | 5.67 | 4.68 × 105 |
| | 24 Hour | $6.2 \times 10^4$ | 4.79 | | |

CFU = Colony Forming Units

TABLE 3

| Neutralization Confirmation Control Results | | | | |
|---|---|---|---|---|
| | | Neutralization Confirmation (CFU) | | |
| Test Substance | Test Organism | Numbers Control | Test Substance Results | Pass/Fail (Log10 Difference) |
| Zinc chloride Lot# A0340879 | *Staphylococcus aureus* (ATCC 6538) | 34, 19 | 15, 13 | Pass (0.28) |

CFU = Colony Forming Units

Results

Table 4 shows test results to evaluate antimicrobial effectiveness on *Staphylococcus aureus* for the experiments of this example. Table 5 shows calculated data for percent and Log 10 reduction of the test results shown in Table 4.

TABLE 4

Test Results For *Staphylococcus aureus*

| Dilution (Volume Plated) | Exposure Time 10 minutes | 2 hours | 6 hours | 24 hours |
|---|---|---|---|---|
| | Number of Survivors | | | |
| Test Substance: 0.1% Zinc Chloride | | | | |
| 100 (1.00 mL) | T, T | 56, 42 | 22, 23 | 4, 3 |
| 100 (0.100 mL) | T, T | 3, 3 | 3, 4 | 0, 0 |
| 101 (0.100 mL) | T, T | 1, 0 | 2, 0 | 0, 0 |
| 102 (0.100 mL) | 66, 69 | 0, 0 | 0, 0 | 0, 0 |
| 103 (0.100 mL) | 9, 19 | 0, 0 | 0, 1 | 0, 0 |
| Test Substance: 0.3% Zinc Chloride | | | | |
| 100 (1.00 mL) | T, T | 0, 2 | 0, 0 | 0, 0 |
| 100 (0.100 mL) | T, T | 0, 0 | 0, 0 | 0, 0 |
| 101 (0.100 mL) | 60, 57 | 0, 0 | 0, 0 | 0, 0 |
| 102 (0.100 mL) | 5, 6 | 0, 0 | 0, 0 | 0, 0 |
| 103 (0.100 mL) | 1, 3 | 0, 0 | 0, 0 | 0, 0 |
| Test Substance: 0.5% Zinc Chloride | | | | |
| 100 (1.00 mL) | T, T | 2, 0 | 0, 0 | 0, 0 |
| 100 (0.100 mL) | T, T | 0, 0 | 0, 0 | 0, 0 |
| 101 (0.100 mL) | 32, 26 | 0, 0 | 0, 0 | 0, 0 |
| 102 (0.100 mL) | 5, 5 | 0, 0 | 0, 0 | 0, 0 |
| 103 (0.100 mL) | 0, 1 | 0, 0 | 0, 0 | 0, 0 |

T = Too Numerous To Count (>300 colonies)
A value of <1 was used in place of zero for calculation purposes.

TABLE 5

Calculated Data For *Staphylococcus aureus*

| Test Substance | Exposure Time | CFU/mL in Test Population Control (Log10) | CFU/mL of Survivors | Log10 Survivors | Percent Reduction | Log10 Reduction |
|---|---|---|---|---|---|---|
| 0.1% Zinc | 10 minutes | | $6.8 \times 10^5$ | 5.83 | None | None |
| Chloride | 2 hours | | $4.9 \times 10^2$ | 2.69 | >99.8% | 2.98 |
| | 6 hours | | $2.3 \times 10^2$ | 2.36 | >99.9% | 3.31 |
| | 24 hours | | $4 \times 10^1$ | 1.60 | 99.99% | 4.07 |
| 0.3% Zinc | 10 minutes | $4.68 \times 10^5$ | $5.9 \times 10^4$ | 4.77 | 87.4% | 0.90 |
| Chloride | 2 hours | (5.67) | $1 \times 10^1$ | 1.00 | >99.99% | 4.67 |
| | 6 hours | | <5 | <0.70 | >99.99% | >4.97 |
| | 24 hours | | <5 | <0.70 | >99.99% | >4.97 |
| 0.5% Zinc | 10 minutes | | $2.9 \times 10^4$ | 4.46 | 93.8% | 1.21 |
| Chloride | 2 hours | | $1 \times 10^1$ | 1.00 | >99.99% | 4.67 |
| | 6 hours | | <5 | <0.70 | >99.99% | >4.97 |
| | 24 hours | | <5 | <0.70 | >99.99% | >4.97 |

CFU = Colony Forming Units

The geometric mean and average log 10 values were used for the population control.

Example 2

Materials and Methods

A suspension of test organism *Staphylococcus aureus* (ATCC 6538) was obtained by adding colonies on tryptic soy agar and 5% Sheep Blood (BAP) with incubation parameters of 35° C.-37° C., aerobic in 0.85% saline to match a 3.0 McFarland standard. The suspension was exposed to a test substance of zinc chloride (4.75 mL) with allograft bone 0.25 g at specified concentrations of 0.3% and 0.5% from a 1% stock solution at specified exposure times of 2 hours, 6 hours, and 24 hours at a temperature of 37±1° C.

Latheen broth and 1% sodium bicarbonate (9.9 mL) were used as a neutralizer. After exposure, an aliquot of the suspension was transferred to the neutralizer and was assayed for survivors. Tables 6-8 show the results of the controls used in this example.

TABLE 6

| Control Results | | |
|---|---|---|
| | Type of Control | Results |
| Purity | *Staphylococcus aureus* (ATCC 6538) | Pure |
| | Neutralizer Sterility Control | No Growth |

TABLE 7

| Test Population Control Results | | | | | |
|---|---|---|---|---|---|
| | | Results | | | |
| Test Organism | Timepoint | CFU/mL | Log10 | Average Log10 | Geometric Mean |
| *Staphylococcus aureus* (ATCC 6538) | $T_0$ | $1.15 \times 10^6$ | 6.06 | 5.83 | 6.76 × 105 |
| | 24 Hour | $3.9 \times 10^5$ | 5.59 | | |

CFU = Colony Forming Units

TABLE 8

| Neutralization Confirmation Control Results | | | | |
|---|---|---|---|---|
| | | Neutralization Confirmation (CFU) | | |
| Test Substance | Test Organism | Numbers Control | Test Substance Results | Pass/Fail (Log10 Difference) |
| Zinc chloride | *Staphylococcus aureus* (ATCC 6538) | 33, 34 | 30, 21 | Pass (0.12) |

CFU = Colony Forming Units

Results

Table 9 shows test results for *Staphylococcus aureus* for the experiments of this example. Table 10 shows calculated data of percent and Log 10 reduction for the test results shown in Table 9.

TABLE 9

| Test Results for *Staphylococcus aureus* | | | | | | | | | |
|---|---|---|---|---|---|---|---|---|---|
| Dilution | Number of Survivors Exposure Time | | | | | | | | |
| (Volume | 2 hours | | | 6 hours | | | 24 hours | | |
| Plated) | Rep 1 | Rep 2 | Rep 3 | Rep 1 | Rep 2 | Rep 3 | Rep 1 | Rep 2 | Rep 3 |
| Test Substance: 0.3% Zinc Chloride with allograft bone | | | | | | | | | |
| $10^0$ (1.00 mL) | T, T | T, T | T, T | T, T | T, T | T, T | 12, 2 | 23, 25 | 8, 7 |
| $10^0$ (0.100 mL) | T, T | T, T | T, T | T, T | T, T | T, T | 0, 4 | 1, 8 | 0, 0 |
| $10^1$ (0.100 mL) | T, T | T, T | T, T | 117, 151 | 210, 224 | 254, 206 | 0, 0 | 1, 1 | 0, 0 |
| $10^2$ (0.100 mL) | 69, 63 | 54, 71 | 85, 101 | 14, 3 | 33, 30 | 25, 32 | 0, 0 | 0, 0 | 0, 0 |
| $10^3$ (0.100 mL) | 8, 9 | 7, 9 | 13, 12 | 1, 1 | 3, 3 | 3, 5 | 0, 0 | 0, 0 | 0, 0 |
| Test Substance: 0.5% Zinc Chloride with allograft bone | | | | | | | | | |
| $10^0$ (1.00 mL) | T, T | T, T | T, T | T, T | T, T | T, T | 9, 15 | 5, 5 | 5, 3 |
| $10^0$ (0.100 mL) | T, T | T, T | T, T | T, T | T, T | T, T | 3, 2 | 0, 1 | 1, 0 |
| $10^1$ (0.100 mL) | T, T | T, T | T, T | 78, 73 | 67, 66 | 68, 59 | 0, 0 | 0, 0 | 0, 0 |
| $10^2$ (0.100 mL) | 74, 70 | 130, 117 | 86, 74 | 6, 4 | 4, 8 | 2, 2 | 0, 0 | 0, 0 | 0, 0 |
| $10^3$ (0.100 mL) | 15, 9 | 11, 17 | 13, 9 | 1, 0 | 0, 0 | 1, 0 | 0, 0 | 0, 0 | 0, 0 |

Rep = Replicate

T = Too Numerous To Count (>300 colonies)

TABLE 10

Calculated Data for *Staphylococcus aureus*

| Test Substance | Exposure Time | CFU/mL in Test Population Control ($Log_{10}$) | CFU/mL of Survivors | $Log_{10}$ Survivors | Geometric Mean (Average $Log_{10}$) | Percent Reduction ($Log_{10}$ Reduction) |
|---|---|---|---|---|---|---|
| 0.3% Zinc | 2 hours | $6.76 \times 10^5$ | $6.6 \times 10^5$ | 5.82 | $7.24 \times 10^5$ | No |
| Chloride | | (5.83) | $6.3 \times 10^5$ | 5.80 | (5.86) | Reduction |
| with | | | $9.3 \times 10^6$ | 5.97 | | |
| allograft | 6 hours | | $1.34 \times 10^5$ | 5.13 | $1.91 \times 10^5$ | 71.7% |
| bone | | | $2.17 \times 10^5$ | 5.34 | (5.28) | (0.55) |
| | | | $2.30 \times 10^5$ | 5.36 | | |
| | 24 hours | | $1.2 \times 10^2$ | 2.08 | $1.32 \times 10^2$ | >99.9% |
| | | | $2.4 \times 10^2$ | 2.38 | (2.12) | (3.71) |
| | | | $8 \times 10^1$ | 1.90 | | |
| 0.5% Zinc | 2 hours | | $7.2 \times 10^5$ | 5.86 | $8.91 \times 10^5$ | No |
| Chloride | | | $1.24 \times 10^6$ | 6.09 | (5.95) | Reduction |
| with | | | $8.0 \times 10^5$ | 5.90 | | |
| allograft | 6 hours | | $7.6 \times 10^5$ | 4.88 | $6.92 \times 10^4$ | 89.8% |
| bone | | | $6.7 \times 10^4$ | 4.83 | (4.84) | (0.99) |
| | | | $6.4 \times 10^4$ | 4.81 | | |
| | 24 hours | | $1.2 \times 10^2$ | 2.08 | $6.17 \times 10^1$ | 99.99% |
| | | | $5 \times 10^1$ | 1.70 | (1.79) | (4.04) |
| | | | $4 \times 10^1$ | 1.60 | | |

CFU = Colony Forming Units

The geometric mean and average logo values were used for the test replicates and population control.

Example 3

Materials and Methods

A suspension of test organism *Staphylococcus aureus* (ATCC 6538) was obtained by adding colonies on tryptic soy agar and 5% Sheep Blood (BAP) with incubation parameters of 35° C.-37° C., aerobic in 0.85% saline to match a 3.0 McFarland standard. The suspension was exposed to a test BioCartilage® from ANTHREX substance of 4.75 mL of zinc chloride at specified concentrations of 0.3% and 0.5% containing 0.25 g BioCartilage® at specified exposure times of 6 hours and 24 hours at a temperature of 37±1° C. Latheen broth and 1% sodium bicarbonate (9.9 mL) were used as a neutralizer.

After exposure, an aliquot of the suspension was transferred to the neutralizer and was assayed for survivors. The suspension was also exposed to a test Amnion Matrix from ANTHREX substance of 9.5 mL of zinc chloride at specified concentrations of 0.3% and 0.5% containing Amnion Matrix (1 count) at specified exposure times of 6 hours and 24 hours at a temperature of 37+−1 C. Latheen broth and 1% sodium bicarbonate (9.9 mL) was used as a neutralizer. After exposure, an aliquot of the suspension was transferred to the neutralizer and was assayed for survivors. A Tables 11-13 show the controls used in this example.

TABLE 11

Control Results

| | Type of Control | Results |
|---|---|---|
| Purity | *Staphylococcus aureus* (ATCC 6538) | Pure |
| | Neutralizer Sterility Control | No Growth |

TABLE 12

Test Population Control Results

| Test Organism | Time Point | Results CFU/mL | Results $Log_{10}$ |
|---|---|---|---|
| *Staphylococcus* | Time Zero | $1.54 \times 10^6$ | 6.19 |
| *aureus* | 24 Hours | $9.8 \times 10^4$ | 4.99 |
| (ATCC 6538) | Average $Log_{10}$: 5.59 Geometric Mean: $3.89 \times 10^5$ | | |

CFU = Colony Forming Units

TABLE 13

Neutralization Confirmation Control Results

| Test Substance | Test Organism | Neutralization Confirmation (CFU) Numbers Control | Neutralization Confirmation (CFU) Test Substance Results | Pass/Fail ($Log_{10}$ Difference) |
|---|---|---|---|---|
| Zinc chloride (with BioCartilage ®) | *Staphylococcus aureus* (ATCC 6538) | 36, 29 | 38, 36 | Pass (−0.05) |
| Zinc chloride (with Amnion Matrix) | | 36, 29 | 59, 46 | Pass (−0.20) |

CFU = Colony Forming Units

Table 14 shows test results for *Staphylococcus aureus* for the BioCartilage® experiments of this example. Table 15 shows test results for *Staphylococcus aureus* for the Amnion Matrix experiments of this example. Table 16 shows calculated data of percent and Log 10 reduction for the test results shown in Table 14. Table 17 shows calculated data of percent and Log 10 reduction for the test results shown in Table 15.

TABLE 14

Shows Test Results For Zinc Chloride (With Biocartilage ®)

| Dilution (Volume Plated) | Test Organism: *Staphylococcus aureus* (ATCC 6538) Number of Survivors Exposure Time: 6 hours Replicate 1 | 6 hours Replicate 2 | 24 hours Replicate 1 | 24 hours Replicate 2 |
|---|---|---|---|---|
| Test Substance: 0.3% Zinc chloride with BioCartilage ® | | | | |
| $10^0$ (1.00 mL) | 35, 42 | 51, 28 | 0, 0 | 0, 0 |
| $10^0$ (0.100 mL) | 0, 0 | 0, 0 | 0, 0 | 0, 0 |
| $10^1$ (0.100 mL) | 0, 0 | 0, 0 | 0, 0 | 0, 0 |
| $10^2$ (0.100 mL) | 0, 0 | 0, 0 | 0, 0 | 0, 0 |
| $10^3$ (0.100 mL) | 0, 0 | 0, 0 | 0, 0 | 0, 0 |
| Test Substance: 0.5% Zinc chloride with BioCartilage ® | | | | |
| $10^0$ (1.00 mL) | 29, 21 | 35, 41 | 0, 0 | 0, 0 |
| $10^0$ (0.100 mL) | 0, 0 | 0, 0 | 0, 0 | 0, 0 |
| $10^1$ (0.100 mL) | 0, 0 | 0, 0 | 0, 0 | 0, 0 |
| $10^2$ (0.100 mL) | 0, 0 | 0, 0 | 0, 0 | 0, 0 |
| $10^3$ (0.100 mL) | 0, 0 | 0, 0 | 0, 0 | 0, 0 |

TABLE 15

Shows Test Results For Zinc Chloride (With Amnion Matrix)

| DILUTION (VOLUME PLATED) | Test Organism: *Staphylococcus aureus* (ATCC 6538) Number of Survivors Exposure Time: 6 hours Replicate 1 | 6 hours Replicate 2 | 24 hours Replicate 1 | 24 hours Replicate 2 |
|---|---|---|---|---|
| Test Substance: 0.3% Zinc chloride with Amnion Matrix | | | | |
| $10^0$ (1.00 mL) | 8, 7 | 19, 18 | 0, 0 | 0, 0 |
| $10^0$ (0.100 mL) | 0, 0 | 0, 0 | 0, 0 | 0, 0 |
| $10^1$ (0.100 mL) | 0, 0 | 0, 0 | 0, 0 | 0, 0 |
| $10^2$ (0.100 mL) | 0, 0 | 0, 0 | 0, 0 | 0, 0 |
| $10^3$ (0.100 mL) | 0, 0 | 0, 0 | 0, 0 | 0, 0 |
| Test Substance: 0.5% Zinc chloride with Amnion Matrix | | | | |
| $10^0$ (1.00 mL) | 84, 74 | 4, 2 | 0, 0 | 0, 0 |
| $10^0$ (0.100 mL) | 0, 0 | 0, 0 | 0, 0 | 0, 0 |
| $10^1$ (0.100 mL) | 0, 0 | 0, 0 | 0, 0 | 0, 0 |
| $10^2$ (0.100 mL) | 0, 0 | 0, 0 | 0, 0 | 0, 0 |
| $10^3$ (0.100 mL) | 0, 0 | 0, 0 | 0, 0 | 0, 0 |

TABLE 16

Calculated Data For Zinc Chloride (With Biocartilage ®)

| Test Substance | Exposure Time | CFU/mL in Test Population Control ($Log_{10}$) | CFU/mL of Survivors | $Log_{10}$ Survivors | Geometric Mean (Average $Log_{10}$) | Percent Reduction ($Log_{10}$ Reduction) |
|---|---|---|---|---|---|---|
| 0.3% Zinc | 6 hours | | $3.9 \times 10^2$ | 2.59 | $3.98 \times 10^2$ | >99.8% |
| chloride | | | $4.0 \times 10^2$ | 2.60 | (2.60) | (2.99) |
| with | 24 hours | $3.89 \times 10^5$ | <5 | <0.70 | <5.01 | >99.99% |
| BioCartilage ® | | | <5 | <0.70 | (<0.70) | (>4.89) |
| 0.5% Zinc | 6 hours | (5.59) | $2.5 \times 10^2$ | 2.40 | $3.09 \times 10^2$ | 99.9% |
| chloride | | | $3.8 \times 10^2$ | 2.58 | (2.49) | (3.10) |
| with | 24 hours | | <5 | <0.70 | <5.01 | >99.99% |
| BioCartilage ® | | | <5 | <0.70 | (<0.70) | (>4.89) |

CFU = Colony Forming Units

A value of <1 was used in place of zero for calculation purposes. The geometric mean and average $\log_{10}$ values were used for the population control. The geometric mean and average $\log_{10}$ values were used for the test replicates to determine reductions.

TABLE 17

Calculated Data For Zinc Chloride (With Amnion Matrix)

| Test Substance | Exposure Time | CFU/mL in Test Population Control ($Log_{10}$) | CFU/mL of Survivors | $Log_{10}$ Survivors | Geometric Mean (Average $Log_{10}$) | Percent Reduction ($Log_{10}$ Reduction) |
|---|---|---|---|---|---|---|
| 0.3% | 6 hours | | $8 \times 10^1$ | 1.90 | $1.23 \times 10^2$ | >99.9% |
| Zinc | | | $1.9 \times 10^2$ | 2.28 | (2.09) | (3.50) |
| chloride | | | | | | |

TABLE 17-continued

| Calculated Data For Zinc Chloride (With Amnion Matrix) | | | | | | |
|---|---|---|---|---|---|---|
| Test Substance | Exposure Time | CFU/mL in Test Population Control ($Log_{10}$) | CFU/mL of Survivors | $Log_{10}$ Survivors | Geometric Mean (Average $Log_{10}$) | Percent Reduction ($Log_{10}$ Reduction) |
| with Amnion | 24 hours | $3.89 \times 10^5$ | <5 | <0.70 | <5.01 (0.70) | >99.99% (>4.89) |
| Matrix | | | <5 | <0.70 | | |
| 0.5% Zinc | 6 hours | (5.59) | $7.9 \times 10^2$ | 2.90 | $1.55 \times 10^2$ (2.19) | >99.9% (3.40) |
| chloride | | | $3 \times 10^1$ | 1.48 | | |
| with Amnion | 24 hours | | <5 | <0.70 | <5.01 (0.70) | >99.99% (>4.89) |
| Matrix | | | <5 | <0.70 | | |

CFU = Colony Forming Units

A value of <1 was used in place of zero for calculation purposes. The geometric mean and average logo values were used for the population control. The geometric mean and average $\log_{10}$ values were used for the test replicates to determine reductions.

Example 4

Bone Graft-TB Infection Protocol

Purpose: To Test the Efficacy of Compounds in Clearing Tuberculosis (TB) in Infected Bones Via Washing Materials:

- Cort/Canc Granules, 5 cc (MTF Biologics, 400061)
- 1M Tris-HCL Solution (Teknova, T5074) 5M NaCl (Prepared in lab)
- Zinc Chloride (Sigma, 793523-100G)
- Zinc Oxide (Sigma, 544906-50G)
- BD BBL MGIT Tubes (BD, 245122)
- BD Bactec MGIT 960 Supplement Kit (BD, 245124)

Protocol

Preparation of Cells:

1. Take 40-50 mL Mtb culture at ~0.2 OD
   a. 39 mL was used
2. Centrifuge 4000 rpm for 10 min
3. Resuspend in equal volume of TriCl pH 7.4 (50 mM)+150 mM NaCl and centrifuge again (discard sup)
4. Repeat step 3 one more time.
5. Resuspend in 20 mL of TrisCl
   a. Resuspended in 20.5 mL Preparation of Bones+*Mycobacterium tuberculosis* (Mtb):

1. Weigh out 0.3 g bone (sterile conditions) per microcentrifuge tube
   a. 0.3 g (+/−0.002 g)
2. Add 0.5-1 mL of Mtb suspension to each tube
   a. 1 mL of Mtb suspension added to each tube
3. Incubate at 37 C on a rotary drum for 1-2 hr
   a. Two tubes were stacked into a 15 mL falcon tube and placed in a rotary drum at speed 4 (might have been too fast, speed 2 used for overnight incubation)
4. Centrifuge for 500 g for 5 min to settle the bone or let them stand
5. Wash twice with 1 mL Tris-HCl with wide-bore tip and centrifugation.
   a. Washed 3 times; 900 uL added each time
   b. After the final wash, 200 uL tip was used to remove any excess residue before eluting in the test compound solution Treatment with Zn:

1. Prepare $ZnCl_2$ (10% and 0.5%) and ZnO (0.05 and 0.5 mg/mL) stocks in Tris-HCL at selected conc.
2. Resuspend the bones in treatment solution and incubate them in the rotary drum for 1 hour and 18-24 hour contact time.
   a. Samples left for ~24 hours, 4 replicates of each (a-d)
   b. In lieu of plating, MGIT was used to assess the presence of TB.
   c. Tubes labeled A1-4, contain 100 uL of the supernatant
   d. Tubes labeled B1-4 contain the bone fragments (extracted using wide-cut 1000 uL tips)

Minimum Inhibitory Concentration (MIC) Assay:

Prepare ZnO stock in 7H9 MIC media at 128 ug/mL and $ZnCl_2$ stock at 10%. Serially dilute 11 concentrations with wide-bore tips (for ZnO)

Results:

1. Alamar Blue plate assay: $ZnCl_2$ MIC 0.0039% (39 ug/mL), ZnO MIC 64 uM
2. Mycobacteria Growth Indicator Tube (MGIT) Assay

TABLE 18

| Effects of Zinc Compound in Inhibiting growth of Mycobacterium tuberculosis (Mtb) (First Round) | | | | |
|---|---|---|---|---|
| Treatment | Bone fraction | Time to positive (Days; hr) | Supernatant Fraction | Time to positive (Days; hr) |
| 0.5% | B1 | 2; 15 | A1 | 6; 08 |
| $ZnCl_2$ | B2 | 2; 8 | A2 | 6; 11 |
| | B3 | 2; 17 | A3 | 6; 16 |
| | B4 | 2; 11 | A4 | 6; 18 |
| 10% | B1 | 9; 21 | A1 | neg (day 18) |
| $ZnCl_2$ | B2 | 12; 16 | A2 | neg (day 18) |
| | B3 | 11; 02 | A3 | 18; 01 |
| | B4 | 1; 07 | A4 | 17; 23 |
| 0.05% | B1 | 2; 06 | A1 | 5; 23 |
| ZnO | B2 | 2; 10 | A2 | 6; 15 |
| | B3 | 2; 09 | A3 | 6; 22 |
| | B4 | 2; 08 | A4 | 6; 17 |
| 0.5% | B1 | 2; 10 | A1 | 5; 20 |
| ZnO | B2 | 2; 12 | A2 | 6; 01 |
| | B3 | 2; 16 | A3 | 5; 23 |
| | B4 | 2; 13 | A4 | 5; 17 |

TABLE 18-continued

Effects of Zinc Compound in Inhibiting growth of Mycobacterium tuberculosis (Mtb) (First Round)

| Treatment | Bone fraction | Time to positive (Days; hr) | Supernatant Fraction | Time to positive (Days; hr) |
|---|---|---|---|---|
| Untreated | B1 | 2; 4 | A1 | 6; 17 |
| | B2 | neg (day 18) | A2 | 7; 4 |
| | B3 | 2; 6 | A3 | 6; 7 |
| | B4 | 2; 9 | A4 | 6; 11 |

Second round results: Repeated experiment with 1% and 5% wash for 20 hr.

The data suggests 5% $ZnCl_2$ wash reduced Mtb load by one log 10 to untreated (use H37Rv dilutions as reference). The time to positive for 5% $ZnCl_2$ treatment of bone fraction increased by one day compared to untreated controls that amount to about one log 10 decrease in Mtb burden. The same is also reflected in the supernatant fractions of 5% treatment.

Table 19. Effects of Zinc Compound in Inhibiting Growth of *Mycobacterium tuberculosis* (Mtb) (Second Round)

The Mtb bound bones were treated for 20 hours in $ZnCl_2$ solution (1 and 5%). Post-treatment, the supernatants were diluted 1:10 before inoculating into MGIT tubes, and bone fractions were washed once to wash off excess $ZnCl_2$.

| Treatment | Bone fraction | Time to positive (Days; hr) | Supernatant Fraction | Time to positive (Days; hr) |
|---|---|---|---|---|
| 5% | B1 | 4; 02 | A1 | 15; 01 |
| ZnCl2 | B2 | 4; 05 | A2 | 15; 01 |
| | B3 | 4; 05 | A3 | 15; 20 |
| | B4 | 4; 05 | A4 | 16; 12 |
| 1% | B1 | 3; 19 | A1 | 10; 02 |
| ZnCl2 | B2 | 3; 18 | A2 | 9; 19 |
| | B3 | 3; 11 | A3 | 12; 10 |
| | B4 | 3; 12 | A4 | 12; 14 |
| Untreated | B1 | 3; 03 | A1 | 13; 05 |
| | B2 | 3; 02 | A2 | 13; 01 |
| | B3 | 2; 23 | A3 | 9; 9 |
| | B4 | 3; 02 | A4 | 9; 12 |
| H37Rv | | | | |
| Neat | | 3; 03 | | |
| e-1 | | 4; 05 | | |
| e-2 | | 5; 13 | | |
| e-3 | | 7; 03 | | |
| e-4 | | 8; 16 | | |
| e-5 | | 10; 09 | | |
| e-6 | | 11; 21 | | |
| e-7 | | neg | | |

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:

1. A method for preparing a bone tissue graft, comprising: providing a bone tissue graft; and applying to the bone tissue graft an antimicrobial solution comprising a zinc compound by contacting the bone tissue graft with the antimicrobial solution for about 10 minutes to about three hours, thereby causing the zinc compound to bond directly to the bone tissue graft and modify the surface of the bone tissue graft, wherein the bone tissue graft surface is contacted with the antimicrobial solution without prior surface modification and the antimicrobial solution exhibits antimicrobial activity of inhibiting or controlling growth of *Mycobacterium tuberculosis* in the bone tissue graft and provides deep tissue cleaning.

2. The method of claim 1, wherein the zinc compound is selected from the group consisting of zinc chloride, zinc sulfate, zinc phosphate, zinc carbonate, and zinc nitrate, zinc chlorate, zinc chromate, and combinations thereof.

3. The method of claim 1, wherein the zinc compound is zinc chloride.

4. The method of claim 1, wherein the zinc compound is a zinc salt selected from Zn acetate, Zn formate, Zn propionate, Zn gluconate, bis(maltolato)Zn, Zn acexamate, Zn aspartate, bis(maltolato)Zn(II) [Zn(ma)2], bis(2-hydroxypyridine-N-oxido)Zn(II) [Zn(hpo)2], bis(allixinato) Zn(II) [Zn(alx)2], bis(6-methyl-picolinato)Zn(II) [Zn(6mpa)2], bis (aspirinato)Zn(II), bis(pyrrole-2-carboxylato) zinc [Zn(pc) 2], bis(alpha-furonic acidato)zinc [Zn(fa)2], bis(thiophene-2-carboxylato) zinc [Zn(tc)2], bis(thiophene-2-acetato)Zn [Zn(ta)2], (N-acetyl-L-cysteinato) Zn(II) [Zn(nac)], Zn(II)/ poly(γ-glutamic acid) [Zn(γ-pga)], bis(pyrrolidine-N-dithiocarbamate) zinc(II) [$Zn(pdc)_2$], Zn(II) L-lactate [$Zn(lac)_2$], Zn(II) D-(2)-quinic acid [$Zn(qui)_2$], bis(1,6-dimethyl-3-hydroxy-5-methoxy-2-pentyl-1,4-dihydropyridine-4-thionato) zinc(II) [Zn(tanm)2], β-alanyl-L-histidinato Zn(II) (AHZ) and combinations thereof.

5. The method of claim 1, wherein the antimicrobial solution comprises $zn^{2+}$ ions.

6. The method of claim 1, wherein the step of contacting the bone tissue graft with the antimicrobial solution comprises soaking, rinsing, or washing the bone tissue graft in the antimicrobial solution.

7. The method of claim 1, wherein the bone tissue graft comprises a tissue selected from allograft bone, autograft bone, xenograft bone, and a combination of two or more thereof.

8. The method of claim 1, wherein the bone tissue graft comprises an allograft bone.

9. The method of claim 1, wherein the step of applying comprises applying to the bone tissue graft the antimicrobial solution comprising from about 1% to about 20% zinc chloride by soaking, rinsing, or washing the bone tissue graft in the antimicrobial solution.

10. The method of claim 1, wherein the step of applying comprises applying to the bone tissue graft the antimicrobial solution comprising from about 5% to about 10% zinc chloride by soaking, rinsing, or washing the bone tissue graft in the antimicrobial solution.

11. The method of claim 1, wherein the antimicrobial solution further comprises a pharmaceutically acceptable vehicle, excipient, diluent, or adjuvant.

12. The method of claim 1, wherein the step of applying comprises applying to the bone tissue graft an antimicrobial solution comprising a zinc compound by contacting the bone tissue graft with the antimicrobial solution for about 10 minutes to about two hours.

13. The method of claim 1, wherein the step of applying comprises applying to the bone tissue graft an antimicrobial solution comprising a zinc compound by contacting the bone tissue graft with the antimicrobial solution for about 10 minutes to about one hour.

14. The method of claim 1, wherein the antimicrobial solution comprises an antimicrobial active consisting essentially of a zinc compound.

15. The method of claim 1, wherein the antimicrobial solution comprises an antimicrobial active consisting of a zinc compound.

* * * * *